United States Patent [19]

Messina et al.

[11] Patent Number: 4,978,786

[45] Date of Patent: Dec. 18, 1990

[54] CHEMICAL PROCESS FOR THE PREPARATION OF OXAMIDE DERIVATIVES AND COMPOUNDS PREPARED THEREBY

[75] Inventors: Giuseppe Messina, Alghero; Giovanni Sechi, Ozieri; Loreno Lorenzoni, Porto Torres; Vittorio Bruzzi, Milan, all of Italy

[73] Assignee: Enichem Anic S.p.A., Palermo, Italy

[21] Appl. No.: 507,084

[22] Filed: Apr. 5, 1990

Related U.S. Application Data

[63] Continuation of Ser. No. 32,554, Apr. 1, 1987, abandoned.

[30] Foreign Application Priority Data

Apr. 17, 1986 [IT] Italy ............................. 20121 A/86

[51] Int. Cl.$^5$ .................. C07C 237/10; C07C 237/08; C07C 237/12; C07C 255/29
[52] U.S. Cl. .................................. 564/160; 558/445; 560/169; 564/153
[58] Field of Search ................ 564/160, 153; 558/445; 560/169

[56] References Cited

U.S. PATENT DOCUMENTS 2,294,878  9/1942  Hummel et al. ............... 564/160 X
2,461,509  2/1949  Harvey et al. ................. 564/160
4,119,615  10/1978  Schulze ......................... 564/160 X

OTHER PUBLICATIONS

Wagner & Zook, *Synthetic Organic Chemistry*, Wiley & Sons, 1953, p. 568.
March, *Advanced Organic Chemistry*, 3rd Ed., Wiley & Sons, 1985, pp. 376–377.

*Primary Examiner*—Carolyn S. Elmore
*Attorney, Agent, or Firm*—Oblon, Spivak, McClelland, Maier & Neustadt

[57] ABSTRACT

A process is described for the preparation of oxamide derivatives wherein one or both —NH$_2$ groups are replaced by primary or secondary amino groups, through reaction of oxamide with a suitably selected amine of formula RR$^1$NH wherein R represents a substituted straight or branched (C$_2$–C$_{12}$)alkyl radical wherein the substituent(s) or at least one of the substituents is selected from the group consisting of hydroxy, amino, mono-substituted amino, and di-substituted amino, and R$^1$ represents hydrogen or an optionally substituted (C$_1$–C$_6$)alkyl radical; representative oxamide derivatives which can thus be obtained useful as corrosion inhibitors, intermediates for polymers, polymer stabilizers, and slow-release fertilizers, are also described.

9 Claims, No Drawings

CHEMICAL PROCESS FOR THE PREPARATION OF OXAMIDE DERIVATIVES AND COMPOUNDS PREPARED THEREBY

This application is continuation Ser. No. 07/032,554 filed on Apr. 1, 1987, now abandoned.

The present invention refers to a process for preparing oxamide derivatives wherein one or both —NH$_2$ groups are replaced by primary or secondary amino groups, the new oxamide derivatives thus obtainable and the use of the obtained products as intermediates for polymers, corrosion inhibitors, polymer stabilizers, and slow-release fertilizers.

A first object of the present invention is a process for the preparation of oxamide derivatives of the following general formula:

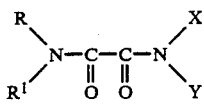   I wherein

R represents a substituted straight or branched (C$_2$–C$_{12}$)alkyl radical wherein the substituent(s) or at least one of the substituents is selected from the group consisting of hydroxy, amino, mono-substituted amino, and di-substituted amino, R$^1$ represents hydrogen or an optionally substituted (C$_1$–C$_6$)alkyl radical, and X and Y are both hydrogen or X is the same as R and Y is the same as R$^1$, through reaction of oxamide with a primary or secondary amine of formula RR$^1$NH wherein R and R$^1$ are as defined above.

Several mono- and di-substituted oxamide derivatives are described in literature (see for instance Berichte 36 p. 1279, JACS 75 (1953) p. 242, Berichte 15 p. 426, U.S. Pat. No. 3,211,562, B.P. Nos. 1,191,609; 1,202,948, 1,213,326, 1,225,671, EP-A-2616).

A general method for the preparation of these compounds, according to the teachings of the above references, consists in the reaction of oxalic acid, or a conventional functional derivative thereof, such as an ester thereof, particularly diethyl oxalate, or an acyl halide, typically oxalyl chloride, with a suitably selected amine.

Said method, however, has remarkable disadvantages, as it does involve the use of highly expensive or very toxic and corrosive reactants (both oxalic acid and oxalyl chloride are in fact very toxic and caustic-see Merck Index 9$^{th}$ Ed. monographs 6743 and 6745); furthermore, the use of such highly reactive starting compounds, easily leads to undesired side-reactions which considerably lower the overall yields.

Improvements in the above general process, involving for instance the use of a particular catalyst and/or of particular reaction conditions (see for instance Russian patent Nos. 706.404 and 732.248) have been set up, and alternative methods, such as for instance the reaction between oxamide and an aromatic hydrocarbon in HF at high temperatures (see DT-OS-2806562), have been devised, but none of these methods has successfully overcome the above summarized disadvantages.

It has now surprisingly been found, and this represents the first object of the present invention, that, when oxamide derivatives of formula I are desired, wherein R, R$^1$, X, and Y are as defined above, they can be prepared, in very high yields, by reacting oxamide with the suitably selected amines of formula RR$^1$NH.

The use of oxamide as the reaction partner overcomes the above drawbacks of the prior art processes, as oxamide is a compound of low reactivity, which is almost devoid of toxic and corrosive properties, easily available and very cheap.

The presence of at least one hydroxy, amino, monosubstituted amino, or di-substituted amino substituent on the alkyl chain of the radical R, is however strictly necessary as, in the absence of such a substitution, the reaction between oxamide and the amine reaction partner does not occur or does not occur to a substantial extent. Thus, for the purposes of the present invention, in the definition of the substituent R, the sentence "substituted (C$_2$–C$_{12}$)alkyl radical wherein the substituent(s) or at least one of the substituents is selected from the group consisting of hydroxy, amino, mono-substituted amino, and di-substituted amino" means that the alkyl radical must bear at least one substituent selected from hydroxy, amino, mono-substituted amino, and di-substituted amino, but may also bear one or more other substituents independently selected from cyano, thio, (C$_1$–C$_6$)alkyl-thio, nitro, carbo(C$_1$–C$_4$)alkoxy, and (C$_1$–C$_6$)alkoxy.

The term "mono-substituted amino" identifies an amino radical wherein one of the hydrogen atoms is replaced by a group selected from straight or branched (C$_1$–C$_6$)alkyl optionally substituted with amino, mono-(C$_1$–C$_6$)alkylamino, di-(C$_1$–C$_6$)alkylamino, amino-(C$_2$–C$_6$)alkylamino, hydroxy, cyano, thio, (C$_1$–C$_6$)alkyl-thio, nitro, carbo(C$_1$–C$_4$)alkoxy or (C$_1$–C$_6$)alkoxy, and (C$_2$–C$_4$)alkanoyl, while the term "di-substituted amino" identifies an amino radical wherein both hydrogen atoms, each independently, are replaced by optionally substituted alkyl or alkanoyl groups as indicated above.

Finally, the term "optionally substituted (C$_1$–C$_6$)alkyl" identifies straight or branched (C$_1$–C$_6$)alkyl radicals optionally substituted with one or more groups selected from amino, mono-(C$_1$–C$_6$)alkylamino, di-(C$_1$–C$_6$)alkylamino, amino-(C$_2$–C$_6$)alkylamino, hydroxy, thio, (C$_1$–C$_6$)alkyl-thio, nitro, cyano, carbo(C$_1$–C$_4$)alkoxy and (C$_1$–C$_6$)alkoxy.

According to a preferred embodiment of the present invention, R is as defined above, wherein the term "mono-substituted amino" identifies an amino radical wherein one of the hydrogen atoms is replaced by an alkyl chain optionally substituted with hydroxy, amino, (C$_1$–C$_6$)alkylamino, and/or amino-(C$_2$–C$_6$)alkyl-amino and "di-substituted amino" designates an amino radical wherein one of the hydrogen atoms is replaced by a (C$_1$–C$_6$)alkyl group and the other is replaced by an alkyl chain optionally substituted with hydroxy, amino, (C$_1$–C$_6$)alkylamino, and/or amino-(C$_2$–C$_6$)alkyl-amino, and R$^1$ is a hydrogen atom.

Oxamide reaction partners of particular interest for the uses of the end products according to the teachings of the present invention, are:

(a) aliphatic diamines or polyamines of formula RR$^1$NH wherein R is a straight or branched (C$_2$–C$_{12}$)alkyl radical bearing at least one substituent selected from amino, mono-(C$_1$–C$_6$)alkylamino, di-(C$_1$–C$_6$)alkylamino, and amino-(C$_2$–C$_6$)alkylamino, and R$^1$ is a straight or branched (C$_1$–C$_6$)alkyl radical, optionally substituted with amino, mono-(C$_1$–C$_6$)alkyl-amino, di-(C$_1$–C$_6$)alkylamino, or amino-$(C_2-C_6)$alkylamino, or, preferably, a hydrogen atom.

Particularly preferred diamines, pertaining to this group, which may suitably be employed in the present process include ethylenediamine, tetramethylenediamine, hexamethylenediamine, diethylenetriamine, and triethylenetetramine.

(b) Aliphatic primary or secondary amines $RR^1NH$ wherein R is a substituted straight or branched $(C_2-C_{12})$alkyl radical bearing at least one hydroxy group, and $R^1$ is an optionally substituted straight or branched $(C_1-C_6)$alkyl chain, or, preferably, a hydrogen atom. Preferred compounds $RR^1NH$ falling within the above definition are ethanolamine, propanolamine, diethanol amine, trihydroxymethylaminomethane, mono-ethanolethylenediamine, etc.

When, in the starting amine reactant, R and/or $R^1$ contain an amino or mono-substituted amino substituent, the obtained condensation product of formula I may react further with oxamide or mono-substituted oxamide to give a dimer which in its turn may react again with oxamide or mono-substituted oxamide and so on, to give a mixture of polymerization products. The process for preparing said di- or poly-oxamides from oxamide and the suitably selected diamine obviously fall within the scope of the present invention.

The reaction of the present invention may be carried out easily by contacting, under stirring, oxamide with a suitable amount of the amine, either in the presence or in the absence of a reaction solvent, at a temperature generally comprised between 20° and 300° C.

When a compound of formula I is desired wherein X and Y are hydrogen, an equimolar amount of amine with regard to the oxamide has to be employed, while, when a bis-substituted oxamide is desired, a molar amount of the amine at least double than that of the oxamide has to be employed, but generally an excess and, more preferably, a strong excess, is employed.

In such a case, the use of a reaction solvent is not strictly necessary, because excess amine itself can act as the solvent, and, preferably, it is avoided. When, however, excess amine cannot be employed, or when the amine to be used has a melting point higher than the optimum reaction temperature, a solvent is conveniently employed. Solvents which can suitable be employed in this reaction are those capable of dissolving both the amine and the amide reaction partners without negatively interfering with the reaction course. Besides water, solvents which may suitably be employed are polar organic solvents either protic or aprotic such as lower aliphatic alcohols, e.g. methanol, ethanol, isopropanol, butanol, and hexanol, aliphatic and cyclic ethers, e.g. ethyl ether, diisopropyl ether, tetrahydrofuran and dioxane, glycols, e.g. ethylene glycol, and propylene glycol, glycol ethers, e.g. ethylene glycol mono-ethyl ether, mono-methyl ether, mono-butyl ether, and dimethyl ether, lower halogenated hydrocarbons, e.g. dichloroethane, chloroform, and methylene chloride, organic acids, e.g. acetic acid, trichloroacetic acid, trifluoroacetic acid and other polar solvents such as dimethylsulfoxide, dimethylformamide, and the like.

The reaction temperature is generally comprised between 20° and 300° C., and is preferably kept between 50° and 150° C. The reaction is generally carried out at atmospheric pressure even if, sometimes, higher pressures may conveniently be employed, particularly when the amine reactants $RR^1NH$ have a low boiling point.

Ammonia gas which forms during the reaction is continuously removed from the reaction medium and ammonia formation is used to monitor the reaction course.

At the end of the reaction, the obtained product is recovered by means of conventional techniques immediately apparent to any skilled chemist. As an example, when low boiling amines are employed, by distilling off the excess amine and the reaction solvent, if any, or, when amines with a very high melting point are employed, by removing the reaction solvent and adding a precipitating solvent capable of dissolving excess amine without dissolving the desired product which is then separated by filtration, decantation or centrifugation. If desired, the thus obtained product can be purified, typically by crystallization.

A further object of the present invention are the novel oxamide derivatives obtainable with the process of the present invention. More particularly, the di- and poly-condensation products of oxamide with the above aliphatic amines are new compounds and represent a further object of the present invention.

These compounds in spite of the fact that they do not contain an aromatic nucleus in their chemical structure, proved to be active as antioxidizing agents.

More particularly, they are active as stabilizers for organic materials against oxidative degradation, chiefly UV-induced degradation. They may be employed alone or in combination with other stabilizers for different materials such as, for instance, stabilizers for textiles of a natural origin either vegetal or animal, fibrous material of a natural origin, natural resins and in particular synthetic polymers and co-polymers, using the application techniques known in this field. They are furthermore useful as corrosion inhibitors, particularly in chemical plants, and as intermediates for polymers, particularly flame-resistant polyurethanes (e.g. French patent Nos. 1,371,391, DT-OS 2,302,579, DT-OS 3,332,792) poly(ester amideurethanes) (e.g. Chem. Abst. 77, 140877f), poly(ether amideurethanes) (e.g. Chem. Abst. 77, 20482b), and regular copolyamides (e.g. U.S. patent application Ser. No. 471,513 May 20 1974). Furthermore, they can be used as slow-release fertilizers.

The use of oxamide as a slow-release fertilizer is known (see for instance Development in Plant and Soil Sciences Vol. 15—Fertilizer Manual—Ed. T. P. Hignett—Martinus Nijhoff/Dr. W. Junk Publishers (1985) p. 279). Owing to its poor water solubility, it is possible, in fact, to control the rate of nitrogen release in available form, as this generally depends not only on the hydrolysis rate or on the rate of microbiological degradation of the product to convert nitrogen into available form, but also on the dissolution rate of the product in the soil. It is also known that in general those fertilizers which contain ammonium nitrogen, such as urea and oxamide which hydrolyse more-or-less easily, in soil, to give ammonia, undergo the microbiological nitrification process which involves conversion of the ammonium form into nitrate. This last form may leach more easily into the soil and, once in the anaerobic layers, be reduced to nitrite which is unstable and decomposes into elemental nitrogen ($N_2$) and $N_2O$ which is lost to the atmosphere (denitrification). In order to overcome this problem, some admixtures of oxamide or oxamide containing fertilizers and nitrification inhibitors have been studied (see Japanese patent application publication No. 6376/72—Derwent Agdoc card 13134T) and the use of oxamide granulated with gypsum, possibly combined with other fertilizers, has been proposed (see Japanese patent application publication No. 6375/72—Derwent Agdoc card 13133T). Di- and poly-condensation products of oxamide with aliphatic diamines, which actually behave as oxamide precursors, and modulate its release and then its use as fertilizer, are therefore suitable, in particular as mixtures of di- and poly-condensation products, for the use as slow-release fertilizers without requiring any particular formulation. For this use a preferred group of novel compounds of the present invention comprises the di- and poly-condensation products of oxamide with primary aliphatic diamines containing 2,3, or 4 carbon atoms, such as ethylenediamine, trimethylenediamine, tetramethylenediamine, and diethylenetriamine, as these may afford a fertilizer with a nitrogen content of about 20–25%. As far as both the formulations of the di-and polycondensation products as soil fertilizers and the application techniques thereof are concerned, the same teachings as for oxamide apply. The following examples describe in detail the process of the invention and some representative compounds obtainable through said process.

EXAMPLE 1

Preparation of N,N'-bis(2-aminoethyl)oxamide $$H_2N-CH_2-CH_2-NH-\underset{\underset{O}{\|}}{C}-\underset{\underset{O}{\|}}{C}-NH-CH_2-CH_2-NH_2$$

A mixture of ethylenediamine (150 ml, 134.25 g, 3.23 mol) and oxamide (24.636 g, 0.279 mol) is charged in a three-necked 250-ml flask equipped with a reflux condenser, a thermometer, a $N_2$ inlet tube and a magnetic stirrer. The reaction mixture is heated to 115° C. and kept at this temperature under stirring for 20 hours.

Ammonia which forms during the reaction is recovered and titrated (8.9 g, theoretical 9.48 g).

At the end of the reaction, excess ethylenediamine is distilled off.

The residue, which consists of a pale, finely divided, solid, is dried at room temperature under vacuum for a few hours in order to remove ethylenediamine completely.

The thus obtained N,N'-bis(2-aminoethyl)oxamide (45 g, 92%) is insoluble in water, alcohols, and most organic solvents, and soluble in mineral and organic acids. Molecular weight, cryoscopically determined, is 180.

Elemental analysis gave the following results:
C: 40.5% w. (calculated=41.37)
H: 8.1% w. (calculated=8.04)
N: 31.4% w. (calculated=32.18)
The I.R. and N.M.R. analyses confirmed the assigned structure.

EXAMPLE 2

Preparation of N,N'-tetrakis(2-hydroxyethyl)oxamide $$\begin{array}{c}HO-CH_2-CH_2\\ \diagdown\\ HO-CH_2-CH_2\end{array}N-\underset{\underset{O}{\|}}{C}-\underset{\underset{O}{\|}}{C}-N\begin{array}{c}\diagup CH_2-CH_2-OH\\ \\ \diagdown CH_2-CH_2-OH\end{array}$$

A mixture of diethanolamine $(NH(CH_2-CH_2-OH)_2)$ (48.0 g, 0.46 mol) and oxamide (10.0 g, 0.11 mol) is charged into a three-necked 100-ml flask equipped with a thermometer, a reflux condenser, a small inlet tube to pass a weak nitrogen stream through the reaction mixture, and a magnetic stirrer. The reaction mixture is kept at 130° C. until ammonia evolution subsides (about 6.5 hours). Ammonia formed during the reaction (3.5 g, corresponding to 90.6% of the theory), is absorbed in HCl and determined by titration.

The reaction mixture (43.3 g) is then distilled under vacuum (from 0.5 to 0.8 mmHg) at 115°–120° C. to remove diethanolamine (19.7 g).

The residue (23.6 g) is a viscous liquid soluble in water, ethyl alcohol and methyl alcohol. The compound, as confirmed by N.M.R., I.R. and elemental analyses, is the N,N'-tetrakis(2-hydroxyethyl)oxamide.

Molecular weight, cryoscopically determined, using acetic acid as the solvent, is 264.

EXAMPLE 3

Preparation of N,N'-bis(2-hydroxyethyl)oxamide $$HO-CH_2-CH_2-NH-\underset{\underset{O}{\|}}{C}-\underset{\underset{O}{\|}}{C}-NH-CH_2-CH_2-OH$$

Monoethanolamine $(NH_2-CH_2-CH_2-OH)$ (150 ml, 2.5 mol) and oxamide (27.47 g, 0.32 mol) are poured into a three-necked 250-ml flask equipped with a thermometer, a reflux condenser, a $N_2$ inlet tube and a magnetic stirrer. The reaction mixture is kept at 120°–130° C. until ammonia evolution subsides (about 6 hours), then it is cooled to room temperature and methanol (about 100 ml) is added. Immediately upon the addition, raw N,N'-bis(2-hydroxyethyl)oxamide precipitates and is recovered by filtration, washed with a small amount of methanol and crystallized from methanol.

A crystalline product (52 g) is obtained which is soluble in cold water, slightly soluble in alcohol, insoluble in ethyl ether and is characterized by m.p. 167°–68° C.

The compound has been characterized by N.M.R. and I.R. analyses. Elemental analysis confirmed the assigned structure.

EXAMPLE 4

Preparation of N,N'-bis(2-hydroxy-1,1-bis-hydroxymethylethyl)oxamide $$\begin{array}{c}HO-CH_2\\ \diagdown\\ HO-CH_2-C-HN\\ \diagup\\ HO-CH_2\end{array}-\underset{\underset{O}{\|}}{C}-\underset{\underset{O}{\|}}{C}-NH-C\begin{array}{c}\diagup CH_2-OH\\ -CH_2-OH\\ \diagdown CH_2-OH\end{array}$$

A mixture of 2-amino-2-hydroxymethyl-1,3-propanediol (13.8 g, 0.114 mol), oxamide (5.0 g, 0.057 mol), and diethylene glycol monomethyl ether (19 g, 18.4 ml) is charged into a three-necked flask equipped with a thermometer and a magnetic stirrer. The reaction mixture is heated to 150° C. and kept at this temperature under a mild nitrogen stream for 12 hours. Ammonia gas evolved during the reaction is absorbed in 1N $H_2SO_4$ and titrated (1.4 g).

The white solid which precipitates from the reaction mixture upon addition of methyl alcohol (75 ml), is collected by filtration (7.5 g) and crystallized to yield the compound of the title as a pure compound. M.p. 210° C. N.M.R. and F.T./I.R. analyses as well as the microanalysis confirmed the assigned structure.

EXAMPLE 5

Preparation of N,N'-bis(3-hydroxypropyl)oxamide

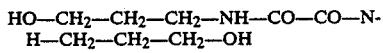

A mixture of 3-amino-1-propanol (150 ml, 1.97 mol) and oxamide (24.16 g, 0.27 mol) is charged into a three-necked 250-ml flask equipped with a thermometer, a reflux condenser, a $N_2$ inlet tube, and a magnetic stirrer. The reaction mixture is heated to 145°–150° C. and kept at this temperature until the evolution of ammonia gas subsides (about 6 hours), then the reaction mixture is cooled to room temperature and methanol (about 50 ml) is added.

The compound of the title which precipitates, is recovered by filtration, washed with a small amount of cold methanol, and crystallized from methanol. The purified compound which is thus obtained has a melting point of 157°–59° C., is soluble in cold water, and poorly soluble in alcohol. The N.M.R. and I.R. analyses as well as the microanalysis confirmed the assigned structure.

We claim:

1. A process for preparing an oxamide derivative of formula I

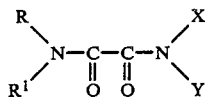

wherein
R represents a substituted straight or branched ($C_2$–$C_{12}$)alkyl radical wherein the substituent(s) or at least one of the substituents is selected from the group consisting of hydroxy, amino, mono-substituted amino, and di-substituted amino,
$R^1$ represents hydrogen or an optionally substituted ($C_1$–$C_6$)alkyl radical, and
X and Y are both hydrogen or X is the same as R and Y is the same as $R^1$,
which comprises reacting oxamide with a primary or secondary amine of formula $RR^1NH$ wherein R and $R^1$ are as defined above, at a temperature of from 20° to 300° C., in the presence or in the absence of a solvent, and continuously removing ammonia which forms; said process being further characterized in that when in the starting amine reactant, R and/or $R^1$ contain an amino or mono-substituted amino substituent, the condensation product of formula I may react with additional oxamide or mono-substituted oxamide giving a di- and/or poly-condensation product thereof.

2. A process as in claim 1 wherein R is a straight or branched ($C_2$–$C_{12}$)alkyl radical bearing at least one substituent selected from hydroxy, amino, mono-($C_1$–$C_6$)alkyl-amino, di-($C_1$–$C_6$)alkyl-amino, and amino($C_2$–$C_6$)alkylamino, and $R^1$ is a hydrogen atom or a straight or branched ($C_1$–$C_6$)alkyl radical, optionally substituted with hydroxy, amino, mono-($C_1$–$C_6$)alkylamino, di-($C_1$–$C_6$)alkyl-amino.

3. A process as in claim 2 wherein $R^1$ is a hydrogen atom.

4. A process as in claim 1 wherein the starting amine of formula $RR^1NH$ is selected from the group consisting of ethylenediamine, tetramethylenediamine, pentamethylenediamine, hexamethylenediamine, diethylenetriamine, triethylenetetramine, ethanolamine, propanolamine, diethanolamine, 2-amino-2-hydroxymethyl-1,3-propanediol and mono-ethanol-ethylenediamine.

5. A process as in claim 1 wherein a di- and/or poly-condensation product of oxamide with the amine is obtained.

6. A process as in any of preceding claims 1 to 5 wherein the amine $RR^1NH$ is used in a large excess.

7. A process as in claim 1 wherein the reaction temperature is between 50° and 150° C.

8. A process as in claim 1 wherein the condensation is carried out in the absence of solvent or in the presence of a solvent selected from water and polar organic solvents.

9. A process as in claim 8 wherein the polar organic solvent is selected from lower aliphatic alcohols, aliphatic and cyclic ethers, glycols, etherate glycols, lower aliphatic hydrocarbons, organic acids, dimethylsulfoxide and dimethylformamide.

* * * * *